United States Patent [19]

Yamaguchi et al.

[11] Patent Number: 5,464,818

[45] Date of Patent: Nov. 7, 1995

[54] PROTEIN HAVING CELL GROWTH-STIMULATING AND MACROPHAGE CHEMOTACTIC ACTIONS, PREPARATIVE METHOD THEREFOR AND USE THEREOF

[75] Inventors: Tadashi Yamaguchi; Hiroshi Uesaka; Kazuo Watanabe; Juichi Awaya, all of Aichi, Japan

[73] Assignee: Sanwa Kagaku Kenkyusho Co., Ltd., Aichi, Japan

[21] Appl. No.: 365,820

[22] Filed: Dec. 29, 1994

[30] Foreign Application Priority Data

Dec. 29, 1993 [JP] Japan ................................. 5-351225

[51] Int. Cl.⁶ ...................... C12P 21/00; A61K 38/00; A61K 38/02
[52] U.S. Cl. ........................ 514/2; 435/71.2; 435/71.3; 435/842; 424/115
[58] Field of Search ............................ 424/115; 514/2; 435/71.3, 71.2, 842

[56] References Cited

U.S. PATENT DOCUMENTS 4,604,234  8/1986  Fujii et al. ................... 514/2

FOREIGN PATENT DOCUMENTS 60-28999  2/1985  Japan.
3-215435  9/1991  Japan.
5-163158  6/1993  Japan.

OTHER PUBLICATIONS

"Cleavage of Structural Proteins during the Assembly of the Head of Bacteriophage T4," Nature vol. 227, Aug. 15, 1970, pp. 680–685, U. K. Laemmli.

"Disc Electrophoresis–II, Method and Application to Human Serum Proteins," Cell Research Laboratory and Department of Hematology, The Mount Sinai Hospital, Baruch J. Davis, pp. 404–427.

"Crystalline Soybean Trypsin Inhibitor–II. General Properties," From the Laboratories of the Rockefeller Institute for Medical Research, Princeton, N.J., Oct. 21, 1946, M. Kunitz.

"The Fluorometric Measurement of Deoxyribonucleic Acid in Animal Tissues with Special Reference to the Central Nervous System," J. Biol. Chem. vol. 233, pp. 184–188, Feb. 7, 1958, John M. Kissane et al.

"The Chemotactic Effect of Mixture of Antibody and Antigen on Polymorphonuclear Leucocytes," J. Exp. Med. vol. 115 (1962), pp. 453–466, Stephen Boyden.

Primary Examiner—Herbert J. Lilling
Attorney, Agent, or Firm—Nikaido, Marmelstein, Murray & Oram

[57] ABSTRACT

There are described a novel protein derived from *Clostridium perfringens* FERM BP-4584 method of obtaining the same and use thereof as an effective ingredient for treating wounds and ulcers. The protein has a molecular weight of 420,000±40,000 by a GPC, isoelectric point of 4.8, and consists of a single subunit having a molecular weight of 130,000±20,000 by a SDS-polyacrylamide gel electrophoresis, and shows cell growth-stimulating activity as well as macrophage chemotactic action. The protein can be extracted and separated by conventional techniques for obtaining a protein from general microorganisms, by taking an inhibition of decomposition into consideration, since the protein is not so stable.

5 Claims, 1 Drawing Sheet

FIG. 1

▲ : Protein according to the invention
(MW : about 420000) derived from
*Clostridium perfringens*
FERM BP-4584

■ : Protein disclosed in Jap. Pat. No.
Hei 5 (A.D. 1993) - 38000(B)
(MW : about 160000) derived from
*Clostridium perfringens*
ATCC 21510

FIG. 2

PROTEIN HAVING CELL GROWTH-STIMULATING AND MACROPHAGE CHEMOTACTIC ACTIONS, PREPARATIVE METHOD THEREFOR AND USE THEREOF

BACKGROUND OF THE INVENTION (1) Field of the Invention

The present invention relates to a novel protein having cell growth-stimulating and macrophage chemotactic actions, a preparative method therefor, and use thereof for treating wounds and ulcers.

(2) Related Arts

In the recent years, the average life expectancy tends to be prolonged, and the medical technology for prolonging life has been improved greatly; however, the situation associated with so-called "bedsores" is becoming more serious as the number of permanently bed-ridden people increases.

In addition, wound diseases including such as skin ulcers and dermatitides from the stresses of life or allergies have lately attracted attention. Such diseases have been considered as not fatal with the exception that the affected parts spread over extensively; therefore, an external preparation such as a skin protecting agent, anti-infective agent, or steroid agent is normally applied locally for the treatment. Examples of such a conventional wound-treating external preparation include a zinc oxide ointment, "Solcoseryl" (Trademark) ointment (an extract from hemolysed blood of young cattle), "Zildasac" (Trademark) ointment (bendazac), "Elase" (Trademark) ointment (fibrinolysin, DNase), "Cartabes" (Trademark) (carbazochrome alkyldiaminoethylglycine hydrochloride), AD ointment (an enforced cod-liver oil), "Alkixa" (Trademark) ointment (aluminum chlorohydroxy allantoinate) and "Oronine" (Trademark) ointment (an analog of chlorohexidine), and the like. However, these treatments are not basic but only symptomatic.

A close look at the tissue disability caused by a would and its repairing process will reveal that the most important elements required for the treatment are the contraction, the epithelization and the formation of granulation tissue; therefore, recent wound-treating drugs are trending towards cell growth-stimulating and tissue repair-accelerating preparations which may be applied clinically.

Typical examples of such a preparation include "Reflap" (Trademark) ointment (lysozyme chlorides), "Olcenon" (Trademark) ointment (tretinoin-tocoferil), "Actosin" (Trademark) ointment (bucladesine sodium), or the like; however, presently available preparations are less than satisfactory and there is a continuing and growing demand for improved types of wound-treating drugs.

In view of the foregoing situation the present inventors have intensively investigated the treatment of wound diseases of skin from various points of view, and as a result, found that hydantoin compounds having aldose reductase-inhibitory action are effective for preventing and treating skin ulcers caused by diabetes complications [Jap. Pat. No. Hei 3 (A.D. 1991)-215435(A)], and kininogenase from human urine are effective for preventing and treating a skin ulcer based on blood flow disorder [Jap. Pat. No. Hei 5 (A.D. 1993)-163158(A)]. In addition, the inventors have found that a protein obtained from the cultured cell body of various strains including genus of Clostridium has cell growth-stimulating action, and an ointment containing the protein exhibits remarkable wound-healing effect on the full-thickness skin wounds model in rats [Jap. Pat. No. Hei 5 (A.D. 1993)-38000(B)].

SUMMARY OF THE INVENTION

Therefore, an object of the invention is to provide a novel wound-treating drug.

The inventors have continued the foregoing investigation of the treatment of wound diseases of skin from every aspect to find a new substance effective for treating wound diseases; and, as a result of random screening various strains for a protein having cell growth-simulating action which is expected to be generally useful for treating wound diseases of skin, found that an unknown protein presents in the cell body extract of a newly isolated strain of *Clostridium perfringens* which was designated by us as "*Clostridium perfringens* 7544S".

The inventors have further investigated the protein produced by the new strain, and found that; the protein is a very high molecular weight substance (MW: about 420,000 determined by a gel permeation chromatography); has proteinase activity and macrophage chemotactic action in addition to cell growth-stimulating action. That is, the protein has a combination of cell growth-stimulating and macrophage chemotactic actions which are useful for treating wound diseases. The invention has been completed on the basis of these findings. The newly found strain which produces the protein of the invention was domestically deposited in Japan at National Institute of Bioscience and Human-Technology Agency of Industrial Science and Technology under FERM P-14028 which has been transferred to international deposition at the international depositary authority under FERM BP-4584.

As a side view of the treatment of wound diseases, the inventors have investigated cell growth-stimulating action for some time in the past, with the result that the evaluation method of the action has now developed to an extent that the action can be evaluated quantitatively.

A detailed investigation conducted by such an evaluation system revealed that the cell growth-stimulating action of the protein according to the invention is remarkably strong and of the order of 50 folds as strong as that exhibited by the previous protein (MW: about 160,000) derived from *Clostridium perfringens* ATCC 21510 and disclosed in said Jap. Pat. No. Hei 5 (A.D. 1993)-38000(B).

Thus, the protein of the invention can exhibit cell growth-stimulating action in vitro test, even when the concentration is several ng/ml to several 10 ng/ml. In addition, the protein also shows macrophage chemotactic action in the concentration range as above; therefore, in connection with wound treatment, it can be said that the protein is a substance more suitable for the wound healing as compared with the protein disclosed in the foregoing Jap. Pat. No. Hei 5 (A.D. 1993)-38000(B).

DETAILED DESCRIPTION OF THE INVENTION

The protein according to the invention is that derived from a newly isolated strain (internationally deposited under FERM BP-4584) of *Clostridium perfringens*, and having following physicochemical, biological and enzymatic characteristics:

(A) Molecular weight; 420,000±40,000, as determined by gel permeation chromatography witch a high-speed liquid chromatography column, (B) Subunit constitution; a single subunit having a molecular weight of 130000±20000, as determined by SDS-polyacrylamide gel electrophoresis, (C) Isoelectric point; 4.8, (D) Internal metal; calcium ion, (E) Electrophoretic characteristics; it shows a single dyed band having an electrophoretic mobility of less than 0.1, when the protein is analyzed by electrophoresis in accordance with the Davis method reported in "Ann. New York Acad. Sci.", Vol. 121, page 404 (1964) at a pH of 8.3, an electric current of 20 mA/gel, for two hours by using a polyacrylamide minislab-gel prepared at a straight concentration gradient of 4 to 20%, (F) Biological activity; cell growth-stimulating action and macrophage chemotactic action, (G) Enzymatic activity: proteinase activity, and (H) Enzymatic properties;
1) the activity decreases in the presence of a serine protease inhibitor,
2) the activity increases in the presence of various metal ions, and
3) the activity is stabilized in the presence of calcium ion.

According to the invention, the foregoing protein can be obtained by the cultivation of the *Clostridium perfringens* FERM BP-4584, followed by extraction and separation thereof from the cultured cell body or the culture medium.

Any conventional process for the extraction, separation and purification of a protein from the cell body may be applied for the method of obtaining the desired protein, but it is necessary to take into account a fact that the protein in question is not so stable. That is, the cell body is first treated with chilled acetone to obtain a dry cell body thereby avoiding autolysis of the cell body, and the dry cell body is then treated ultrasonically or by a homogenizer, preferably crushed under pressure in order to carry out the crushing rapidly, after which the protein is extracted.

The crushing of the cell body and the extraction of protein may preferably be carried out in the presence of calcium ion to maintain the protein in a stable state. Upon completion of crushing cell body and extraction of protein, the extract is centrifuged to remove insoluble debris such as cell walls, nuclei and others, thereby providing a clear supernatant fraction. The nucleic acid-containing supernatant fraction is then treated with a conventional denucleating agent such as protamine sulfate to give a denucleated fraction.

The denucleated extract is further treated by column chromatography, such as ion exchange chromatography, gel filtration chromatography, hydroxyapatite chromatography or hydrophobic interaction chromatography, which has been used in the conventional purification of proteins, in order to eliminate sugar components and other proteins derived from the cell body, foreign proteins and residual protamine sulfate. Thus the fraction which contains the protein of interest can be fractionated.

Ion exchange chromatography is particularly useful as the first treating step. Any commercially available gel may be used as the column carrier such as DEAE-Sepharose CL-6B or CM Sepharose CL-6B (available from Pharmacia Aktiebolag, Sweden); however, in any case, it is preferred to employ a calcium ioncontaining buffer solution to stablize the protein of the invention.

The protein according to the invention becomes unstable in the isolated state, and is rendered inactive as the purification progresses; therefore, the column chromatography is preferably carried out at a temperature below 10° C. In this case, the employment of a high-performance liquid chromatographic (HPLC) apparatus fitted with a HPLC column is recommended to carry out the purification as quickly as possible;

The purification of the protein should be carried out to such an extent that a partially purified protein product can be obtained wherein the impurities are present in an amount within the stability range of the protein and within a pharmaceutically acceptable and innoxious range.

Thus, according to the first aspect of the invention, there is provided a pharmaceutical composition which comprises the foregoing protein as an active ingredient and a pharmaceutically acceptable carrier.

The composition is used for the treatment of diseases such as wounds, gastic and leg ulcers in such a field that the acceleration of cell proliferation is effective.

It is desirable to employ the protein in a purified state, especially for internal use, if possible; however, the protein which contains impurities in an amount within a pharmaceutically acceptable range may be also used because the protein of the present invention becomes unstable as the purification of the protein proceeds.

The protein compositions used for the foregoing purposes are preferably in the form of external or internal use. Examples of the compositions for external use include ointments aqueous pharmaceuticals, suspension pharmaceuticals, eye drops, suppositories, and the like. Among them, most preferred ones for use in treating wounds are ointments.

Examples of the bases which can be employed for preparing ointments include conventional bases such as white vaseline, purified lanolins, liquid paraffins, polyethylene glycols, higher-fatty alcohols, and vegetable oils.

Any conventional method for preparing ointments may be employed.

Although the amount of pharmaceutical composition of the invention in these preparations will depend upon the kind of the preparations, the optimum amount is normally, e.g., about 0.0025 to 0.08% by weight for ointments.

A zinc compound may be preferably blended in ointments to improve the wound-healing effect.

Examples of such zinc compounds include zinc oxide, fatty acid zinc salts, zinc salts of organic acid, zinc salt of inorganic acid, e.g., zinc stearate, zinc lactate, zinc acetate, zinc chloride, and the like. Among them are preferably zinc oxide, zinc salt of fatty acid such as zinc stearate; and zinc salt of organic acid such as zinc lactate and zinc acetate. Zinc oxide and fatty acid zinc salts are particularly preferred.

The suitable weight ratio of the pharmaceutical composition of the invention to the zinc compound, e.g., zinc oxide will fall within the range of from 1:2000 to 8000.

The suitable weight ratio of the composition to the zinc salt of fatty acid will fall within the range of from 1:400 to 4000.

It is recommended to apply the ointment on the skin once to several times per day.

A conventional wetting agent, stabilizer, antiseptic or gelling agent may be blended to the ointment to further improve the quality.

In the preparation of pharmaceutical compositions for internal use of the protein of the invention, the resulting preparations are in the form of tablet, powder, capsule, aqueous solution or suspension, and the like. Any conventional base or preparative method may be utilized.

Although the dose of protein according to the invention depends on the region or size of the particular wound, the optimum dose for internal use is normally 50 mg to 2 g/day for an adult, which is preferably taken orally in two to three installments.

A 10% aqueous protein solution can be obtained with ease by dissolving the protein in water. Aqueous or suspension preparations for internal or external use or eye drops can be prepared by using the aqueous protein solution.

BRIEF DESCRIPTION OF THE DRAWINGS

FIG. 1 is a graph showing cell growth-stimulating action of the protein according to the invention, in comparison with that of the known protein [MW: 160000, Jap. Pat. No. Hei 5 (A.D. 1993)-38000(B)] derived from *Clostridium perfringens* ATCC 21510; and FIG. 2 is a graph showing results of investigations on macrophage chemotactic action of the protein according to the invention by the Boyden's chamber method.

DETAILED DESCRIPTION OF PREFERRED EMBODIMENTS

The invention will now be explained with reference to following Examples.

Preparative Example (1) Cultivation of strain

A newly isolated strain of *Clostridium perfringens* designated as *Clostridium perfringens* 7544S (internationally deposited under "*Clostridium perfringens* FERM BP-4584"), was lyophilized and stored.

The strain was taken out from a vial for storage, and transplanted to a GYPC culture medium (10 ml) already sterilized in an autoclave. Renaturing cultivation (37° C., 20 hours) of the strain was carried out under anaerobic conditions. The renatured strain suspension (10 ml) was then inoculated onto a GYPC (400 ml) already sterilized, after which enrichment cultivation was conducted under anaerobic conditions ( 37° C., 20 hours).

The resulting enriched suspension of cultured cells was transferred to a culture vessel (200 liters), inoculated onto a GYPC culture medium (200 liters) already sterilized in an autoclave, after which the cells were cultivated at 37° C. under nitrogen atmosphere.

After initiation of cultivation, turbidity of the cultivated strain-containing suspension was periodically measured at 660 nm by a Hitachi 100-20 type spectrophotometer manufactured by Hitachi Ltd.

When steady state had been observed by 4 to 6 hours after initiation of cultivation, the suspension was treated on a continuous centrifuge at 15000 rpm and thereby providing living strains. The living strains thus obtained were washed with 0.9% NaCl solution (300 ml), and then suspended thoroughly in chilled acetone (3 liters), after which the acetone was removed by filtration. The resultant strain body was dried, and a dry body (130 g) was obtained.

Results of the identification test on the culture medium (200 liters) show that the strain belongs to the genus of *Clostridium perfringens*.

(2) Extraction from strain body

The foregoing dry strain body (3 kg) was suspended in 0.02M Tris-HCl buffer (pH 8.0, 200 liters) containing 2 mM $CaCl_2$, after which the strain body was crushed at 450 $kg/cm^2$ by feeding the suspension to a high-pressure crusher. The lysate was centrifuged at 8000×g for 30 minutes and, thereby collecting a supernatant. To the supernatant was added aqueous 8% protamine sulfate solution (pH 7.0, 1 liter), and it was stirred at 4° C. for 15 minutes to denucleate.

The denucleated solution was centifuged at 4° C. and 8000×g, for 30 minutes thereby providing a supernatant as crude extract. As a result of these procedures, it became possible to recognize that the resultant crude extract exhibited cell growth-stimulating action.

(3) Preparation of a partially purified protein product having cell growth-stimulating action All of the following procedures was conducted in a room kept at 4° C.

The foregoing crude extract was adsorbed onto a DEAE Sepharose CL-6B column (diameter of 37 cm×length of 30 cm) already cleaned and equilibrated with 20 mM Tris-HCl buffer (pH 8.0) containing 2 mM $CaCl_2$. After the non-adsorbed components were removed, it was confirmed that the absorbance at 280 nm had been decreased sufficiently. The adsorbed proteins were then eluted with 20 mM Tris-HCl buffer (pH: 8.0) containing 0.2M NaCl-2 mM $CaCl_2$, thereby collecting fractions having cell growth-stimulating action. The protein component in the fractions was concentrated on an ultrafilter (available from Asahi Chemical Industry Co., Ltd.) having a molecular weight exclusion limit of 50,000.

The concentrate thus obtained was desalted by ultrafiltration by adding cold distilled water, after which the fully desalted concentrate was dialyzed against distilled water at 4° C. in a dialysis tube. After insolubles were removed, the dialyzed solution was lyophilized thereby yielding lyophilized powder (about 100 g/3 kg dry strain body).

The resulting partially purified product was provided for preparing preparations and used as an active ingredient of the ointment in Pharmacological Test Example 3.

(4) Protein purification (alternative method)

All of the following procedures was performed with a buffer containing calcium at 4° C. or in an ice-cooled atmosphere.

Onto a DEAE-Sepharose CL-6B column (diameter of 37 mm×length of 30 cm) already equilibrated with 20 mM Tris-buffer solution (pH 8.0) containing 2 mM $CaCl_2$ was adsorbed the crude extract which has obtained in the foregoing Item (2). After the non-adsorbed parts were removed by washing with the same buffer, it was confirmed that the absorbance at 280 nm had been sufficiently decreased. Elution was conducted with 20 mM Tris-buffer solution (pH: 8.0) containing 0.2M NaCl-2 mM $CaCl_2$ thereby collecting fractions having cell growth-stimulating action. A concentrated protein solution was obtained by use of an ultrafiltration membrane (available from Fuji Filter Co., Ltd.) having a molecular weight exclusion limit of 100,000. The concentrated solution was applied to a Sephacryl S-300HR column (diameter of 5 cm×length of 90 cm, available from Pharmacia Aktiebolag, Sweden) for gel filtration and, thereby collecting an active fraction eluted at a molecular weight region of from 400,000 to 450,000. The protein in the fraction was further concentrated by ultrafiltration apparatus (exclusion limit of 30,000, Fuji Filter Co., Ltd.).

The purification procedures were hereinafter carried out quickly by HPLC to increase the separating ability and to prevent a decrease in activity of the :protein. That is, the concentrated active fraction was absorbed onto a TSKgel HA-1000 hydroxyapatite column (21.5×150 mm, available from Toso Co., Ltd.), and the absorbed components were eluted by a linear concentration gradient of 1 to 400 mM of sodium phosphate buffer (pH 6.8). Active fractions were then collected and absorbed onto a Mono Q HR10/10 ion exchange column (10×100 mm, marketed from Pharmacia Aktiebolag, Sweden), and the absorbed components were eluted by a linear concentration gradient of 50 to 250 mM of NaCl.

The active fraction was further absorbed on the foregoing TSKgel HA-1000 hydroxyapatite column, after which the absorbed components were further eluted by a linear concentration gradient of 1 to 200 mM of sodium phosphate buffer (pH 6.8).

The active fraction was concentrated with the aid of on a "Centriprep" (Trademark) centrifugal ultraconcentrator (marketed from Amicon Co., Ltd.) having a molecular weight exclusion limit of 30,000. The concentrated fraction was finally made to flow through a TSKgel G3000SW (21.5×600 mm, available from Toso Co., Ltd.) GPC column already equilibrated with 20 mM Bis-Tris-HCl buffer (pH 6.8) containing 0.1M NaCl-0.1 mM $CaCl_2$, thereby collecting main protein fraction having cell growth-stimulating activity which eluted in a molecular weight region over 400,000. After being added with 20% glycerol the concentrate was lyophilized and stored as a final purified protein product.

The purified product was provided for the identification of physico-chemical, biological and enzymatic characteristics of the protein, as well as for tests in vitro (Pharmacological Test Examples 1 and 2).

(5) Physico-chemical properties

The physico-chemical properties of the cell growth-stimulating protein are as follows:

(A) Molecular weight

A 625LC system HPLC (available from Waters Co., Ltd.) with a TSKgel G4000SWXL GPC column (diameter of 7.8 mm×length of 300 mm, available from Toso Co., Ltd.) was employed for analyzing the protein. The column had been equilibrated with 0.1M NaCl -containing 0.05M phosphoride buffer (pH 6.8).

Separately, β-galactosidase (MW: 465,000), glutamic acid dehydrogenase (MW: 290,000), lactic acid dehydrogenase (MW: 142,000), enolase (MW: 67,000), adenylate kinase (MW: 32,000), and cytochrome C (MW: 12,400) as molecular weight markers were analyzed under the same conditions as above for calibration, and the molecular weight of the protein in question was found to be about 420,000 (probable error: ±40,000), wherein the molecular weight was calculated from the linear regression formula representing a relation between the retention time and molecular weight.

(B) Subunit constitution

The protein was analyzed by SDS-polyacrylamide gel electrophoresis on a 10% polyacrylamide gel by the Laemmli's method, as reported in "Nature", Vol. 227, page 680 (1970). Separately, myosin (MW: 212,000), $\alpha_2$-macroglobulin (MW: 170,000), β-galactosidase (MW: 116,000), transferrin (MW: 76,000), glutamic acid dehydrogenase (MW: 53,000) as molecular weight markers were analyzed under the same conditions as above for calibration.

The molecular weight of the protein in question was calculated from the linear regression formula representing the relation between mobility and molecular weight. The protein in the gel was dyed with Coomassie brilliant blue R-250.

The protein showed a single dyed band having a molecular weight of 130,000 (probable error: ±20,000), indicating that the minimum unit of the peptide linkage of the protein was a subunit having a molecular weight of about 130,000.

(C) Isoelectric point

The protein was analyzed on a carrier-free isoelectric focusing electrophoresis apparatus "Rotofor" (Trademark, available from Bio-Rad Lab.). A pH gradient-forming reagent "Bio-Lyte" (trademark, pH 3.0–10.0) (Bio-Rad Lab.) was employed. Upon completion of isoelectric fractionation, the whole was divided into 20 fractions, and each fraction was measured for its pH, protein concentration, proteinase activity, and cell growth-stimulating activity. The protein concentration, proteinase activity and cell growth-stimulating activity were all present in the same fraction of pH 4.8, and thus its isoelectric point was 4.8.

(D) Amino acid composition

The protein was hydrolyzed with 6N HCl at 110° C. for 24 or 48 hours, and the hydrolysis products were analyzed on a Hitachi L-8500 type high-speed amino acid analyzer manufactured by Hitachi Ltd.

As for cysteine, after the protein was oxidized with performic acid to convert it to cysteinic acid, the above hydrolysis was carried out under the same conditions to prepare a specimen. The amino acid composition thus determined is given in following Table 1.

The results in Table 1 show that most numerous amino acids which constitute the cell growth-stimulating protein of the invention are asparagine/aspartic acids, and lysine, and glutamine/glutamic acids are next in order of numbers. The protein is characterized in that the proportion of cysteine is a very small in quantity, tryptophan cannot be detected by this method.

TABLE 1

| Amino acid | Constitution | |
|---|---|---|
| | μ mol/mg protein | mol/M subunit |
| Asx | 1.165 | 151 |
| Thr | 0.362 | 47 |
| Ser | 0.433 | 56 |
| Glx | 0.684 | 89 |
| Pro | 0.274 | 36 |
| Gly | 0.594 | 77 |
| Ala | 0.508 | 66 |
| Cys | 0.027 | 4 |
| Val | 0.567 | 74 |
| Met | 0.115 | 15 |
| Ile | 0.445 | 58 |
| Leu | 0.541 | 70 |
| Tyr | 0.234 | 30 |
| Phe | 0.194 | 25 |
| Lys | 0.767 | 100 |
| Hys | 0.069 | 9 |
| Arg | 0.091 | 12 |
| Trp | N.D. | N.D. |

N.D.: not detected (E) Constituent metallic ion

A Hitachi 180-80 type polarization Zeeman atomic-absorption photometer (available from Hitachi Ltd.) was employed for analyzing metallic ions possibly presenting in the protein molecule. The results are given in following Table 2.

Four calcium atoms per one subunit having a molecular weight of about 130,000 were detected. Neither magnesium nor zinc was detected.

TABLE 2

| Metal ions | Nos. of metal ions/one molecule-subunit |
|---|---|
| $Ca^{2+}$ | 4.3 |
| $Mg^{2+}$ | 0.1 or less |
| $Zn^{2+}$ | 0.1 or less |

(F) Electrophoretic characteristics

The electrophoresis of the protein was carried out by using a polyacrylamide minislab-gel prepared in a linear concentration gradient of 4 to 20% by the Davis method reported in "Ann. New York Acad. Sci.", Vol. 121, page 404

(1964) under conditions of pH 8.3 and 20 mA/gel for 2 hours. Coomassie brilliant blue R-250 was used for dyeing the protein in the gel. The protein showed a single dyed band with a mobility of 0.07.

(6) Enzymatic characteristics

It has been found that the cell growth-stimulating protein according to the invention has proteinase activity which is highly related with the biological activity. The enzymatic properties of the activity were as follows:

(A) Response to natural substrates (proteins)

Responses of the protein to casein, bovine serum albumin, collagen, bovine γ-globulin, and egg lysozyme were investigated. Results given in following Table 3 show that the protein does not hydrolyzed none other than casein.

TABLE 3

| Natural substrates | hydrolyzed or not |
|---|---|
| Casein | + |
| Bovine serum albumin | − |
| Collagen | − |
| γ-Globulin, | − |
| Lysozyme | − |

(B) Response to synthetic fluorescent substrates

Responses of the protein to synthetic fluorescent substrates were investigated. Results given in following Table 4 show that the protein selectively hydrolyzed synthetic substrates having an aromatic amino acid group in its C-terminus. The response to succinyl-alanyl-alanyl-prolyl-phenylalanine-4-methyl-coumaryl-7-amide was particularly high.

TABLE 4

| Synthetic substrates | Rate of hydrolysis (nmol/min/ml) |
|---|---|
| Suc—Ala—Ala—Pro—Phe—MCA | 175 |
| Suc—Leu—Leu—Val—Try—MCA | 15 |
| Suc—Ile—Ile—Trp—MCA | 1 |
| Suc—Ala—Pro—Ala—MCA | 0 |
| Suc—Ala—Glu—MCA | 0 |
| Suc—Gly—Pro—Leu—Gly—Pro—MCA | 0 |
| Suc(OMe)—Ala—Ala—Pro—Val—MCA | 0 |
| Ac—Tyr—Val—Ala—Asp—MCA | 0 |
| Boc—Val—Leu—Lys—MCA | 0 |
| Pro—Phe—Arg—MCA | 0 |
| Ala—MCA | 0 |
| Leu—MCA | 0 |
| Met—MCA | 0 |
| Phe—MCA | 0 |

(C) Optimum pH for casein-hydrolyzing activity

Casein-hydrolyzing activity of the protein was measured by Kunitz method reported in "J. Gen. Physiol.", Vol. 30, page 291 (1947). The optimum pH was found to be 8.0.

(D) Kinetic analysis of synthetic substrate-hydrolyzing activity

Suc-Ala-Ala-Pro-Phe-MCA was selected as a substrate of the B5 protein, and the optimum pH was found to be 6.2 to 7.0. The measured kinetic constants of the substrate are given in following Table 5.

TABLE 5

| Substrate | Suc—Ala—Ala—Pro—Phe—MCA |
|---|---|
| Optimum pH | 6.2–7.0 |
| Km (mM) | 4.2 |
| Vmax (μ mol/min/mg) | 230 |

(E) Inhibitors for the enzymatic activity

Suc-Ala-Ala-Pro-Phe-MCA was selected as a substrate of the protein, and effect of various enzyme-inhibitors on the enzymatic activity of the protein in question was investigated. Results given in following Table 6 show that diisopropyl fluorophosphoric acid which is a serine enzyme-inhibitor, toluene sulfonylfluoride, and ethylenediaminetetraacetic acid which is a metal chelating agent exhibit a strong inhibitory action.

TABLE 6

| Inhibitory substances | Conc. | Residual activity |
|---|---|---|
| Diisopropyl fluorophosphoric acid | 0.1 mM | 21% |
| Toluene sulfonylfluoride | 0.1 mM | 1% |
| Iodoacetic acid | 0.1 mM | 100% |
| Chymostatin | 0.01 mM | 62% |
| Elastatinal | 0.01 mM | 98% |
| Pepstatin A | 0.01 mM | 103% |
| Aprotinin | 0.1 mM | 55% |
| Soy bean trypsin inhibitor | 0.1 mg/ml | 111% |
| Ethylenediamine tetraacetic acid | 1.0 mM | 34% |
| o-Phenanthroline | 1.0 mM | 85% |

(7-A) Effect of metal ion to activity Suc-Ala-Ala-Pro-Phe-MCA was selected as a substrate of the protein, and effect of various metal ions to the enzymatic activity of the protein was investigated. Results given in following Table 7 show that although all these metal ions may increase the activity, Fe and Zn ions in particular, followed by Ca and Mg ions exhibit a remarked action in that order.

TABLE 7

| Metallic ion | Concentration (mM) | Relative activity (%) |
|---|---|---|
| No added | — | 100 |
| $Na^+$ | 10 | 112 |
| $K^+$ | 10 | 105 |
| $Mg^{2+}$ | 1 | 129 |
|  | 10 | 183 |
| $Ca^{2+}$ | 1 | 136 |
|  | 10 | 196 |
| $Fe^{2+}$ | 1 | 154 |
| $Fe^{3+}$ | 1 | 169 |
| $Cu^{2+}$ | 1 | 108 |
| $Zn^{2+}$ | 1 | 168 |

(7-B) Effect of metal ion to stability

Suc-Ala-Ala-Pro-Phe-MCA was selected as a substrate of the protein, and effect of various metal ions to stability of the protein was investigated in terms of the enzymatic activity. That is, the residual activity after reacting the protein with various concentrations of the metal ion at 37° C. for 4 hours. Results given in following Table 8 show that Na and K ions do not have any effect in 10 mM, and Fe, Cu and Zn ions impaire the stability of protein. Ca ion has a stabilizing effect on the protein.

TABLE 8

| Metallic ion | Concentration (mM) | Residual activity (%) |
|---|---|---|
| No added | — | 59 |
| $Na^+$ | 10 | 67 |
| $K^+$ | 10 | 66 |
| $Mg^{2+}$ | 1 | 65 |
| $Ca^{2+}$ | 1 | 85 |
| $Fe^{2+}$ | 1 | 14 |
| $Fe^{3+}$ | 1 | 17 |
| $Cu^{2+}$ | 1 | 1 |
| $Zn^{2+}$ | 1 | 2 |

Pharmacological Test Example 1

(Cell growth-stimulating action)

The cell growth-stimulating action of the protein was evaluated by cell culture system based on BHK-21 (C-13) cells. After cultivating the cells for 3 days in a $CO_2$ incubator (5% $CO_2$/95% air atmosphere) at 37° C. Eagle MEM culture medium containing 10% bovine fetal serum, the cells were plated on 96-wells microplate in a rate of 1200 cells/well. After cultivating for further 24 hours, the cells were used for testing.

The protein according to the invention was diluted with Eagle MEM culture medium containing 10% bovine fetal serum. After the culture medium of the foregoing 96-wells microplate was exchanged for the culture medium containing the protein in question, the cells were incubated in the $CO_2$ incubator for further two days. After removing the culture medium, the cells were washed with PBS (0.9% NaCl-containing phosphate buffer), fixed with 0.5N trichloroacetic acid solution, and washed with ethyl alcohol and dried.

The cell proliferation activity was measured by using 3,5-diaminobenzoic acid by the DNA quantitative analytical method reported by Kissane, J. M. and Robins, E. in "J. Biol. Chem.", Vol. 238, page 184 (1958).

As a result, it was confirmed that the cell growth-stimulating protein according to the invention can further stimulate the growth of the BHK-21(C-13) cells proliferating in the Eagle MEM culture medium containing 10% bovine fetal serum.

In addition, it was then found that the cell growth-stimulating activity of the protein was about 50 folds than that of the other protein (MW: 160000) derived from *Clostridium perfringens* ATCC 21510 which has been disclosed in Jap. Pat. No. Hei 5 (A.D. 1993)-38000(B) (see FIG. 1).

Pharmacological Test Example 2

(Macrophage chemotactic action)

Macrophage chemotactic action of the protein according to the invention was evaluated with macrophages collected from the mouse peritoneal exudate by the Boyden's chamber method [Boyden, S. "J. Exp. Med.", Vol. 115, page 453 (1962)].

A C3H/He male mouse (5–6 weeks old) received an injection of 10% proteose peptone, intraperitoneally. Macrophages were collected after dehematizing 4 days later. The collected macrophages were suspended in RPMI 1640 culture medium containing 0.5% bovine serum albumin, and resulting cell suspension ($1.5 \times 10^6$ cells/ml) was provided for testing.

The protein was provided for testing as a sample solution which was prepared by dilution with RPMI 1640 culture medium containing 0.5% bovine serum albumin.

The cell suspension (200 µl) and sample solution were charged in an upper chamber and lower chamber of the Boyden's chamber partitioned by a membrane of "CHEMO-TAXICELL" (Trademark, pore size: 5 µm, available from Kurabo Ind. Ltd.). After incubation in a $CO_2$ incubator (5% $CO_2$, 95% air) at 37° C. for 90 min., the cells which have migrated through the membrane were dyed, and the number of dyed cells was counted microscopically (×400).

As a result, the protein exhibited positive chemiotaxis (see FIG. 2).

Pharmacological Test Example 3

(Clinical effect on skin ulcers)

The clinical usefulness of a preparation prepared by using the protein, as an effective ingredient, was investigated, and the clinical usefulness was confirmed as follows:

(1) Determination of optimum dose

Comparative tests were conducted on 256 patients to determine the optimum concentration of protein in an ointment by the double blind method.

The respective patients were sufferers from a skin ulcer [such as a crus ulcer, ambustion ulcer, traumatic ulcer, cruris ulcer (including varicose complex)], and other ulcers (such as sequelae of zoster herpes, radiation ulcer, diabetic ulcer, postoperative ulcer, and the like).

The patients were divided into four groups from (P) to (H), and the optimum concentration was determined by prescribing the following dose of the protein to respective patients of each group for four weeks.

Group P: dose of ointment base,

Group L: dose by low concentration,

Group M: dose by medium concentration,

Group H: dose by high concentration.

Results given in following Table 9 show that the ointment containing the protein is useful for treating the skin ulcers, and the optimum concentration is 0.01% by weight (i.e. the dose by medium concentration for Group M).

TABLE 9

| Gr. | A Very useful | B Useful | C Fairly useful | D No definite answer | E Not desirable | A + B (%) |
|---|---|---|---|---|---|---|
| P | 20 | 16 | 16 | 8 | 6 | 54.5 |
| L | 19 | 18 | 12 | 12 | 2 | 58.7 |
| M | 27 | 24 | 4 | 7 | 2 | 79.7 |
| H | 25 | 20 | 7 | 10 | 1 | 71.4 |

(2) Long-term application test

A long-term application test by the open method was conducted on 279 patients for evaluating effectiveness and safety of the ointment containing the protein of the invention at the foregoing optimum concentration of 0.01% by weight. The patients had been afflicted with an inveterate skin ulcer, and were subjects of over four weeks hospital treatment. The test schedule was as follows:

Test duration was 12 weeks in principle; when the patient had recovered from the ulcer, the application was stopped at that point; however, the application could be continued when the usefulness of the protein was confirmed and the particular patient wished a continuation of the application.

Results given in following Table 10 show that the protein has sufficient safety for a long-term application to a sufferer from an inveterate skin ulcer.

TABLE 10

| A Very useful | B Useful | C Fairly useful | D No definite answer | E Not desirable | A + B (%) |
|---|---|---|---|---|---|
| 141 | 60 | 36 | 25 | 17 | 72.0 |

Medicine Preparation Example

An ointment was prepared in a conventional manner by using following ingredients.

| | |
|---|---|
| Partially purified protein [by Item (3) in Preparative Example] | 10 (mg) |
| White vaseline | 72.5 (g) |
| Liquid paraffin | 10 (g) |

| | |
|---|---|
| bleached bees wax | 10 (g) |
| zinc stearate | 7.5 (g) |

What is claimed is:

1. A protein derived from a newly isolated strain of *Clostridium perfringens* FERM BP-4584 and having following physicochemical, biological and enzymatic characteristics:
   (A) Molecular weight; 420,000±40,000, as determined by gel permeation chromatography with a high-speed liquid chromatography column,
   (B) Subunit constitution; a single subunit having a molecular weight of 130,000±20,000, as determined by SDS-polyacrylamide gel electrophoresis,
   (C) Isoelectric point; 4.8,
   (D) Internal metal; calcium ion,
   (E) Electrophoretic characteristics; it shows a single dyed band having an electrophoretic mobility of less than 0.1, when the protein is analyzed by electrophoresis in accordance with the Davis method at a pH of 8.3, an electric current of 20 mA/gel, for two hours by using a polyacrylamide minislab-gel prepared at a straight concentration gradient of 4 to 20%,
   (F) Biological activity; cell growth-stimulating action and macrophage chemotactic action,
   (G) Enzymatic activity: proteinase activity, and
   (H) Enzymatic properties;
      1) the activity decreases in the presence of a serine protease inhibitor,
      2) the activity increases in the presence of various metal ions, and
      3) the activity is stabilized in the presence of calcium ion.

2. A composition for stimulating cell proliferation (growth), which comprises, in addition to a pharmaceutically acceptable carrier, a protein derived from a newly isolated strain of *Clostridium perfringens* FERM BP-4584 and having following physicochemical, biological and enzymatic characteristics:
   (A) Molecular weight; 420,000±40,000, as determined by gel permeation chromatography with a high-speed liquid chromatography column,
   (B) Subunit constitution; a single subunit having a molecular weight of 130,000±20,000, as determined by SDS-polyacrylamide gel electrophoresis,
   (C) Isoelectric point; 4.8,
   (D) Internal metal; calcium ion,
   (E) Electrophoretic characteristics; it shows a single dyed band having an electrophoretic mobility of less than 0.1, when the protein is analyzed by electrophoresis in accordance with the Davis method at a pH of 8.3, an electric current of 20 mA/gel, for two hours by using a polyacrylamide minislab-gel prepared at a straight concentration gradient of 4 to 20%,
   (F) Biological activity; cell growth-stimulating action and macrophage chemotactic action,
   (G) Enzymatic activity: proteinase activity, and
   (H) Enzymatic properties;
      1) the activity decreases in the presence of a serine protease inhibitor,
      2) the activity increases in the presence of various metal ions, and
      3) the activity is stabilized in the presence of calcium ion.

3. A method for treating wounds and ulcers comprising administering to a mammal in need thereof an effective amount of the composition of claim 2.

4. The method of claim 3 wherein the composition is a preparation for external use.

5. The method of claim 4 wherein the composition is an ointment.

* * * * *